(12) United States Patent
White et al.

(10) Patent No.: US 8,251,060 B2
(45) Date of Patent: Aug. 28, 2012

(54) DEVICE AND METHOD FOR DELIVERING AN AEROSOL DRUG

(75) Inventors: Jackie L. White, Pfafftown, NC (US); Thomas A. Perfetti, Winston-Salem, NC (US)

(73) Assignees: Perfetti and Perfetti, LLC, Winston-Salem, NC (US); William B. Line, Winston-Salem, NC (US)

( * ) Notice: Subject to any disclaimer, the term of this patent is extended or adjusted under 35 U.S.C. 154(b) by 1320 days.

(21) Appl. No.: 11/903,342

(22) Filed: Sep. 21, 2007

(65) Prior Publication Data

US 2008/0110454 A1 May 15, 2008

Related U.S. Application Data

(60) Provisional application No. 60/859,430, filed on Nov. 15, 2006.

(51) Int. Cl.
*A61M 15/00* (2006.01)
(52) U.S. Cl. .............. 128/203.26; 128/203.12
(58) Field of Classification Search .......... 128/200.14–200.22, 202.21, 203.12, 128/203.15–203.17, 203.23, 203.26, 203.27; 131/273, 359
See application file for complete search history.

(56) References Cited

U.S. PATENT DOCUMENTS

| | | | | |
|---|---|---|---|---|
| 4,714,082 A | * | 12/1987 | Banerjee et al. | 131/359 |
| 4,756,318 A | * | 7/1988 | Clearman et al. | 131/359 |
| 4,771,795 A | | 9/1988 | White et al. | |
| 4,819,665 A | | 4/1989 | Roberts et al. | |
| 5,388,572 A | | 2/1995 | Mulhauser et al. | |
| 5,388,573 A | * | 2/1995 | Mulhauser et al. | 128/203.15 |
| 5,388,574 A | | 2/1995 | Ingebrethsen | |
| 5,460,173 A | | 10/1995 | Mulhauser et al. | |
| 5,553,607 A | * | 9/1996 | Chiu et al. | 128/203.26 |
| 6,164,287 A | | 12/2000 | White | |
| 7,090,830 B2 | | 8/2006 | Hale et al. | |
| 2004/0099269 A1 | * | 5/2004 | Hale et al. | 128/203.16 |
| 2007/0062526 A1 | * | 3/2007 | Schuster et al. | 128/203.26 |

FOREIGN PATENT DOCUMENTS

| | | |
|---|---|---|
| DE | 198 54 008 A1 | 5/2000 |
| WO | WO 99/63844 | 12/1999 |
| WO | WO 03/082031 A1 | 10/2003 |

OTHER PUBLICATIONS

Smith et al.; Percutaneous penetration enhancers in cigarette mainstream smoke; Food and Chemical Toxicology 42 (2004) 9-15.
The BOPP Group; BOPP Metal Filter Cloth (product specifications and properties); 2002.

* cited by examiner

*Primary Examiner* — Justine Yu
*Assistant Examiner* — Valerie L Skorupa
(74) *Attorney, Agent, or Firm* — Christopher C. Dremann, P.C.

(57) ABSTRACT

A device and method for delivering a therapeutic drug to a patient in the form of an aerosol includes a heat generating chamber and an aerosol forming chamber separated by a heat conductor. A heating element is disposed within the heat generating chamber in heat conducting relation with the heat conductor. A substrate having a therapeutic drug and an aerosol forming agent deposited thereon is disposed within the aerosol forming chamber in heat conducting relation with the heat conductor. The heating element ignites a fuel source consisting essentially of a combustible liquefied gas to generate heat that is conducted to the heat conductor and then to the substrate via the heat conductor. The heat generated by the heating element activates the aerosol forming agent to volatilize the therapeutic drug into an aerosol drug contained within the aerosol forming chamber and made available to be inhaled by the patient.

20 Claims, 4 Drawing Sheets

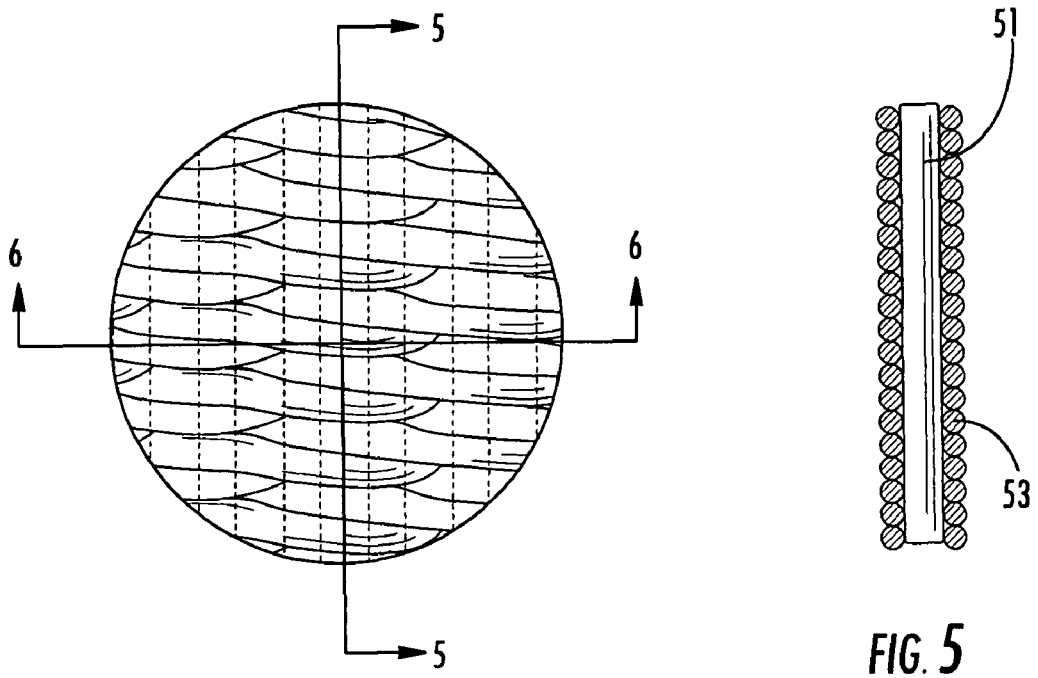
FIG. 4
FIG. 5
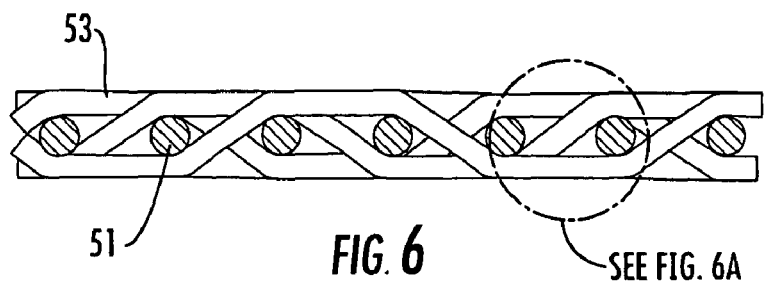
FIG. 6
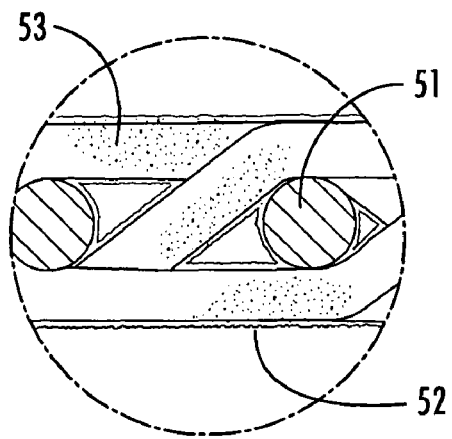
FIG. 6A

DEVICE AND METHOD FOR DELIVERING AN AEROSOL DRUG

CROSS-REFERENCE TO RELATED APPLICATIONS

This application claims the benefit of U.S. Provisional Patent Application No. 60/859,430 filed on Nov. 15, 2006.

BACKGROUND OF THE INVENTION

1. Field of the Invention

The present invention relates generally to a device and method for delivering an aerosol drug. More specifically, the invention is an improved device and method for delivering an aerosol drug to a patient in a more effective and convenient manner.

2. Description of the Related Art

Therapeutic drugs are most commonly delivered to a patient via an oral dosage, such as a pill, capsule or tablet, or via an intravenous solution. Oral dosage forms of drug delivery require a longer time before the effects of the drug are realized by the patient. In addition, drugs delivered to a patient in oral dosage form suffer from a loss of therapeutic effect due to hepatic metabolism. Intravenous drug delivery can be painful and is generally inconvenient for patients not resident in a health care facility. Inhalation drug delivery overcomes the disadvantages of both oral dosage delivery and intravenous drug delivery, but has yet to gain wide acceptance and use. One possible reason for the limited role of inhalation drug delivery, despite its increased efficacy and convenience, is the lack of a suitable device and method for simple, reliable and repeatable delivery of the drug in an aerosol form to the patient. Existing devices for delivering an aerosol drug are suitable for use with only a limited class of therapeutic agents, such as drugs for the treatment of asthma, or are not sufficiently portable, repeatable, reliable or simple to use.

Accordingly, a device for delivering an aerosol drug is needed that is both effective and convenient to use. Such as a device must be capable of delivering a wide range of drugs to a patient in the form of an aerosol in a portable, repeatable, reliable and simple manner. As used herein, the term "aerosol" is intended to include vapors, gases, fine particles, and the like, both visible and invisible, generated by a heat source acting upon an aerosol forming means in a manner according to the invention as described herein. As so defined, the term "aerosol" specifically includes any pharmacologically or physiologically active agents, and any desired additives, such as an aerosol forming agent, irrespective of whether they produce a visible aerosol. As used herein, the term "in heat conducting relation" is intended to mean a physical arrangement of two or more components whereby heat is transferred by conduction or convection from a heat generating source (e.g., heating element) to a thermally conductive component (e.g., heat conductor and/or substrate) substantially throughout the heat generating period of the heat source. A heat conducting relation can be achieved by locating the components in direct physical contact or in close proximity to one another while the heat source operates to generate heat.

BRIEF SUMMARY OF THE INVENTION

To achieve the foregoing and other objects, and in accordance with the purposes of the invention as broadly described herein, the present invention provides a device and method for delivering an aerosol drug to a patient. In the various embodiments, the improved aerosol drug delivery device provides an effective and convenient means for simply, reliably and repeatedly delivering a wide range of drugs to a patient in an aerosol form.

In one aspect, the invention is embodied by a device for delivering a therapeutic drug to a patient in the form of an aerosol. Broadly, the device includes a heat conductor, a heat generating chamber having an open first end and a second end essentially closed by the heat conductor, and an aerosol forming chamber having an open first end and a second end adjacent the second end of the heat generating chamber that is likewise essentially closed by the heat conductor. The device further includes a heating element disposed within the heat generating chamber and positioned in heat conducting relation to the heat conductor. A substrate is disposed within the aerosol forming chamber and positioned in heat conducting relation to the heat conductor.

In preferred embodiments, the substrate supports at least a therapeutic drug and an aerosol forming agent, and the heating element is activated by a fuel source consisting essentially of a combustible liquefied gas to generate heat. The combustible liquefied gas is selected from liquefied petroleum gas (LPG or LP-gas), propane, propylene, butylenes, butane, isobutene, methyl propane and n-butane. The substrate may be any non-combustible, heat conductive material. In one preferred embodiment, the substrate is a woven wire mesh with the therapeutic drug and the aerosol forming agent deposited onto the wire. The aerosol forming agent is a polyol and preferably is selected from glycerin, glycerol, propylene glycol, 1,3-butylene glycol, triethylene glycol, glycryl esters, such as triacetin, propylene carbonate, and mixtures thereof. The therapeutic drug may be any heat stable pharmaceutical having less than about 10% alteration and/or degradation under normal transport and storage conditions.

In another aspect, the invention is embodied by an aerosol drug delivery device including a vessel having a heat generating chamber and an aerosol forming chamber separated by a heat conductor. A heating element is disposed within the heat generating chamber in heat conducting relation to the heat conductor. A substrate is disposed within the aerosol forming chamber in heat conducting relation to the heat conductor. The substrate supports a therapeutic drug and an aerosol forming agent. The heating element generates heat from a fuel source consisting essentially of a combustible liquefied gas and the heat generated by the heating element activates the aerosol forming agent to volatilize the therapeutic drug from the substrate into the form of an aerosol drug. In operation, a patient places the substrate having the therapeutic drug and aerosol forming agent deposited thereon within the aerosol forming chamber and in heat conducting relation to the heat conductor. Preferably, the substrate is positioned in direct contact with the heat conductor. The heating element is positioned within the heat generating chamber in heat conducting relation with the heat conductor. Preferably, the heating element is positioned immediately adjacent, but spaced slightly apart from, the heat conductor. The heating element is then ignited using the combustible liquefied gas to generate heat within the heat generating chamber. The heat generated by the heating element is conducted by the heat conductor to the substrate to activate the aerosol forming agent and thereby volatilize the therapeutic drug deposited on the substrate into the form of an aerosol drug. The aerosol drug within the aerosol forming chamber is then inhaled by the patient.

In yet another aspect, the invention is embodied by a method for delivering a therapeutic drug to a patient in the form of an aerosol. The method includes providing a heat generating chamber and an aerosol forming chamber separated by a heat conductor. The method further includes disposing a heating element within the heat generating chamber in heat conducting relation with the heat conductor. The method further includes disposing a substrate comprising the therapeutic drug and an aerosol forming agent within the aerosol forming chamber in heat conducting relation with the heat conductor. The method further includes igniting the heating element to generate heat from a fuel source consisting essentially of a combustible liquefied gas. The method further includes conducting the heat generated by the heating element through the heat conductor to the substrate. The method further includes heat-activating the aerosol forming agent on the substrate to volatilize an aerosol drug from the therapeutic drug and the aerosol forming agent that is released into the aerosol forming chamber and made available to the patient to be inhaled.

BRIEF DESCRIPTION OF THE DRAWINGS

These and other features, aspects and advantages of the present invention are better understood when the following detailed description of the invention is read in conjunction with the accompanying drawings, in which:

FIG. 4 is a top plan view showing an alternative embodiment of a substrate having a therapeutic drug and an aerosol forming agent deposited thereon for use with the device for delivering an aerosol drug of FIG. 1.

FIG. 5 is a sectional view of the substrate of FIG. 4 taken along the line 5-5 shown in FIG. 4.

FIG. 6 is a sectional view of the substrate of FIG. 4 taken along the line 6-6 shown in FIG. 4.

FIG. 6A is a detail view of a portion of the substrate of FIG. 4 taken from the area indicated in FIG. 6.

DETAILED DESCRIPTION OF THE INVENTION

The present invention will now be described more fully hereinafter with reference to the accompanying drawings in which exemplary embodiments of the invention are shown. However, the invention may be embodied in many different forms and should not be construed as limited to the embodiments set forth herein. The exemplary embodiments are provided so that this disclosure will fully and completely convey the scope of the invention so that one of ordinary skill in the art will be enabled to make, use and practice the invention without undue experimentation. Like reference numbers refer to like elements throughout the various drawings.

The exemplary embodiments shown and described herein provide a device and method for delivering a therapeutic drug to a patient in an aerosol form. As used herein, the term "aerosol" is intended to include vapors, dense gases, fine suspended particles, and the like, both visible and invisible. As so defined, "aerosol" specifically includes any pharmacologically or physiologically active agents, and any desired additives, such as an aerosol forming agent, irrespective of whether they produce a visible aerosol. Ideally, the aerosol has a density consistent with cigarette smoke and a small particle size on the order of about 0.2-3.0 microns. As used herein, the term "aerosol drug" or "drug aerosol" refers to a therapeutic drug in the form of an aerosol and made available for delivery to a patient for use in an inhalation therapy. The aerosol is preferably formed by an aerosol forming agent activated by heat generated by a heating element and conducted by a heat conductor in a manner according to the invention described herein. The device and the aerosol, including the aerosol drug provides an inhalation therapy that is more effective and convenient than other known means for drug delivery.

Figure 1:
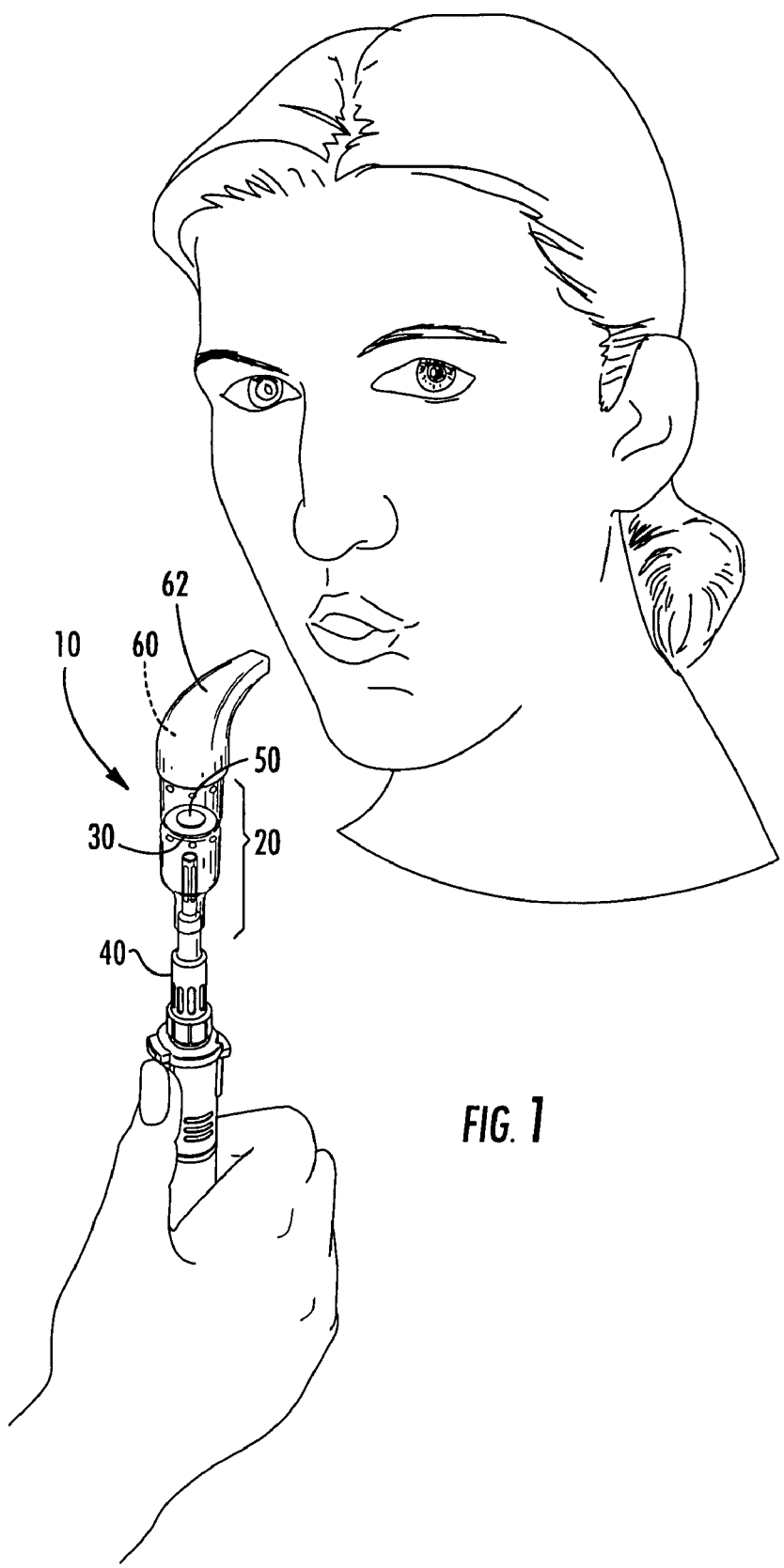
FIG. 1 is an environmental perspective view of an exemplary embodiment of a device for delivering a therapeutic drug in an aerosol form according to the present invention illustrating a patient utilizing the device to inhale an aerosol drug.
Figure 2:
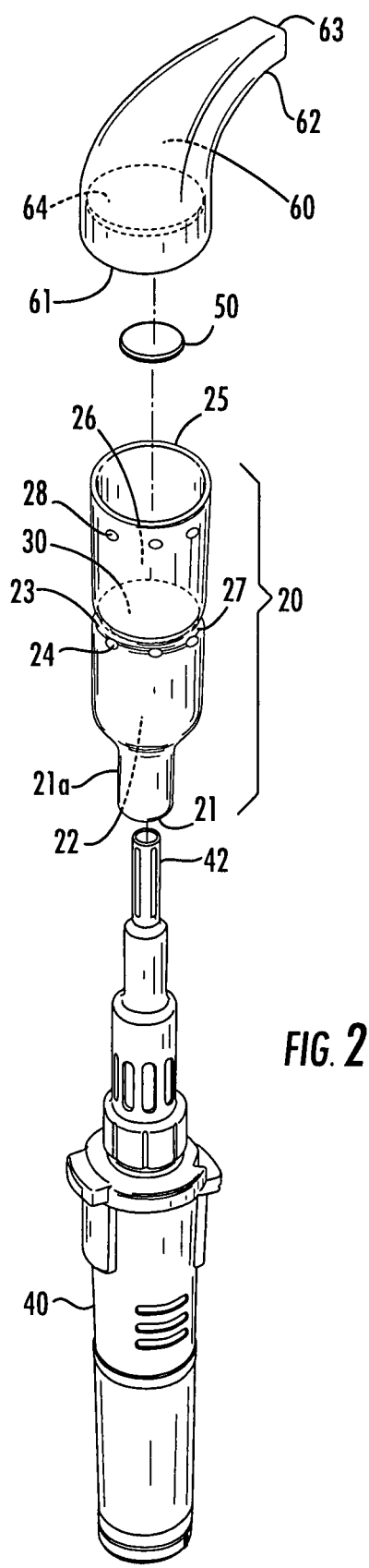
FIG. 2 is an exploded perspective view showing the device for delivering an aerosol drug of FIG. 1 disassembled.
Figure 3:
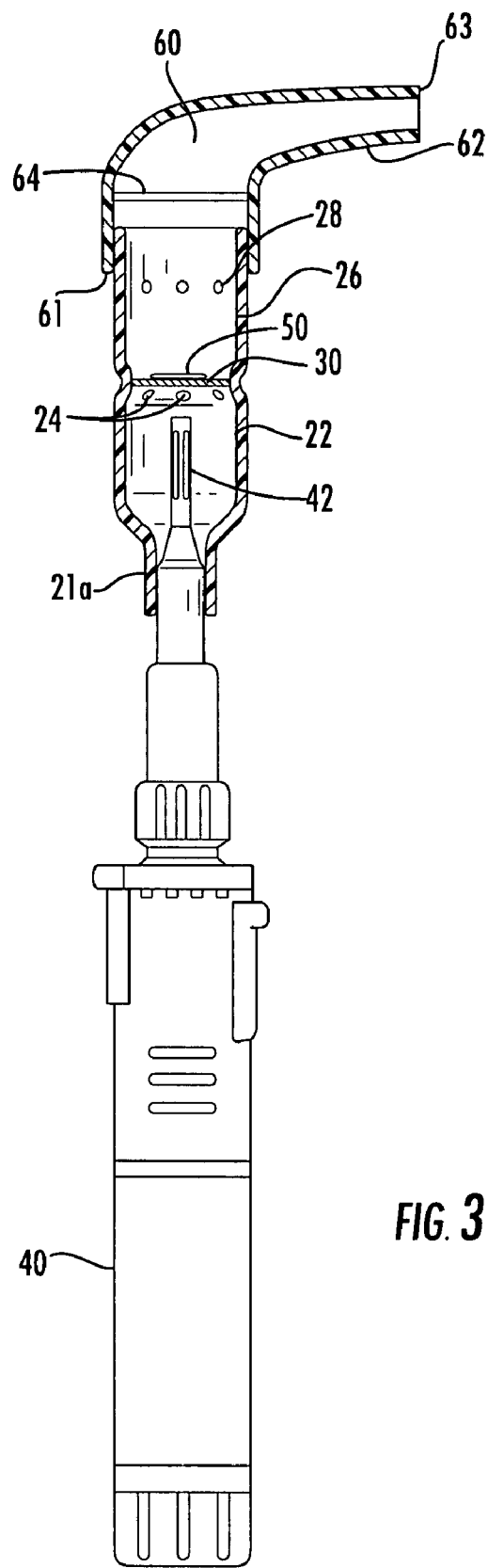
FIG. 3 is a partial cross-sectional view showing the device for delivering an aerosol drug of FIG. 1 assembled.

An environmental perspective view of an exemplary embodiment of a device 10 for delivering an aerosol drug to a patient is shown in FIG. 1. An exploded perspective view of the device 10 disassembled is shown in FIG. 2, and a partial cross-sectional (and partial perspective) view of the device 10 assembled is shown in FIG. 3. The device 10 (also referred to herein as the aerosol drug delivery device 10) comprises a vessel 20 defining a heat generating chamber 22 and an aerosol forming chamber 26. The heat generating chamber 22 has an open first end 21 and a second end 23 opposite the first end. The open first end 21 of the heat generating chamber 22 is sized to receive a heating element 40, which will be described in greater detail hereinafter. As shown, the heat generating chamber 22 is a generally hollow cylinder having a relatively thin wall thickness. Thus, the open first end 21 and the second end 23 are generally circular in radial cross-section. However, the heat generating chamber 22 may have any desired shape suitable for receiving the heating element 40 through the open first end 21 in a loose or slight interference fit. Alternatively, the heat generating chamber 22 and the heating element 40 may be integrally formed or fitted together and sealed in a relatively tight interference fit so that the device 10 may be provided to a patient in a fully assembled condition that is disposable following a predetermined number of uses. However, as will be readily appreciated, the preferred embodiment of the heating element 40 is configured to be removable from the heat generating chamber 22 for convenient storage as well as for the purpose of replacing the expendable heating element, as needed. The second end 23 of the heat generating chamber 22 is essentially closed by a heat conductor 30, as will be described in greater detail hereinafter.

The heating element 40 is disposed within the heat generating chamber 22 in heat conducting relation with the heat conductor 30. In other words, the tip 42 of the heating element 40 is in direct physical contact with the heat conductor 30, or is immediately adjacent (but not in direct physical contact with) the heat conductor, so that heat (i.e., thermal energy) generated by the heating element within the heat generating chamber 22 is conducted by the heat conductor into the aerosol forming chamber 26, as will be further described. Preferably, the tip 42 of the heating element 40 is slightly spaced apart from the heat conductor 30 so that the heating element and/or the heat conductor are not damaged and the tip of the heating element is not obstructed when the heating element is received through the open first end 21 and disposed within the heat generating chamber 22. The heat generating chamber 22 further has at least one, and preferably, a plurality of relatively small air vents 24 therethrough to permit combustion gases created by heating element 40 to be expelled into the surrounding environment and absorbed by the ambient air. In a preferred embodiment, the air vents 24 may be circular openings having a diameter of about 1/16 of an inch. Such a configuration permits the heating element 40 to be in direct contact with, close to, or adjacent the heat conductor 30, so as to provide a heat conducting relation between the heating element and the heat conductor during use of the device 10 to deliver an aerosol drug to a patient. Thus, heat transfer to the heat conductor 30 and the resultant production of the aerosol drug is maximized, as will be described hereinafter. Because the therapeutic drug and the aerosol forming agent are physically separated from the heating element 40, they are exposed to a lower temperature than that generated by the heating element within the heat generating chamber 22, thereby reducing the possibility of thermal degradation of the therapeutic drug.

The heating element 40 may also be contained within an insulating member (not shown) to protect the hand of the patient from the high temperatures generated by the heating element. Insulating members which can be employed in practicing the invention are preferably formed into a porous, resilient jacket formed from one or more layers of an insulating material. Preferably, the insulating member extends over substantially the entire outer periphery of the heating element 40. Insulating materials which can be used in accordance with the present invention generally comprise inorganic or organic fibers such as those made out of glass, alumina, silica, vitreous materials, mineral wool, carbons, silicon, boron, organic polymers, cellulosics, and the like, including mixtures of these materials. Nonfibrous insulating materials, such as silica aerogel, pearlite, glass, and the like, formed in mats, strips or other shapes can also be used. Preferred insulating materials should have a softening temperature above about 650° C. and should not burn, char, decompose or otherwise degrade during use. Preferred insulating materials for the heating element 40 include ceramic fibers, such as glass fibers available from the Manning Paper Company of Troy, N.Y., under the commercial designations Manniglas 1000 and Manniglas 1200.

The aerosol forming chamber 26 likewise has an open first end 25 and a second end 27 opposite the first end. The open first end 25 of the aerosol forming chamber 26 is sized to receive a substrate 50 to be described hereinafter and to operatively engage the mouth of the patient. Alternatively, the open first end 25 may be sized to receive the substrate 50 and to operatively engage an optional aerosol delivery chamber 60 comprising a mouthpiece 62 sized to conform to the mouth of the patient. The optional aerosol delivery chamber 60 positions the mouthpiece 62, and therefore the mouth of the patient, a farther distance from the heating element 40 and the substrate 50, thereby reducing the temperature and diluting the concentration of the aerosol drug. The second end 27 of the aerosol forming chamber 26 likewise is essentially closed by the heat conductor 30, as will be described in greater detail hereinafter. As shown, the aerosol forming chamber 26 is a generally hollow cylinder having a relatively thin wall thickness. Thus, the open first end 25 and the second end 27 are generally circular in radial cross-section. However, the aerosol forming chamber 26 may have any desired shape suitable for receiving the substrate 50 through the open first end 25, and if utilized, the optional aerosol delivery chamber 60. The aerosol forming chamber 26 further has at least one, and preferably, a plurality of relatively small air inlets 28 therethrough to permit ambient air from the surrounding environment to be drawn into the aerosol forming chamber, and thereby assist in circulating and transporting the aerosol drug to the mouth of the patient. In a preferred embodiment, the air inlets 28 may be circular openings having a diameter of about 1/16 of an inch.

If utilized, the open first end 61 of the aerosol delivery chamber 60 is sized and shaped to engage the open first end 25 of the aerosol forming chamber 26 in a relatively tight interference fit. Alternatively, a sealing arrangement (not shown) may be provided between the first end 25 of the aerosol forming chamber 26 and the first end 61 of the aerosol delivery chamber 60 in a conventional manner. As will be readily appreciated, the aerosol delivery chamber 60 is intended to be removable from the aerosol forming chamber 26 for convenient storage, as well as for the purpose of replacing the expendable substrate 50, as needed. The optional aerosol delivery chamber 60 is generally hollow and has a relatively thin wall thickness which transitions smoothly from the open first end 61 to the mouthpiece 62 at the open second end 63. Preferably, the mouthpiece 62 is formed to be comfortably positioned within the mouth and between the closed lips of the patient. An optional particle filter 64 may be disposed anywhere between the heat conductor 30 and the open first end 25 of the aerosol forming chamber 26. In the event the aerosol delivery chamber 60 is utilized, the optional particle filter 64 may be positioned anywhere between the heat conductor 30 and the mouthpiece 62. As shown by way of example only, the optional particle filter 64 is disposed medially between the open first end 25 of the aerosol forming chamber 26 and the mouthpiece 62. Preferably, the particle filter 64 comprises a screen configured to prevent the passage of particulate matter having a mean diameter greater than about 20 microns. In particular, the particle filter 64 is intended to filter any un-volatilized particles of the therapeutic drug and/or aerosol forming agent and any combustion by-products and gases, such as carbon monoxide, that may have been drawn into the aerosol forming chamber 26 through air inlets 28 after being expelled from the heat generating chamber 22 through air passages 24.

In a preferred embodiment, the vessel 20 and the heat conductor 30 are formed from a conventional fritted disc of the type commonly used in physical science and chemistry laboratories to perform evaporation or precipitation. For example, the vessel 20 and the heat conductor 30 may be a Pyrex® glass fritted disc of the type available from Sigma-Aldrich Company of St. Louis, Mo. or from R&H Filter Co., Inc. of Georgetown, Del. "Pyrex" is a registered trademark belonging to Corning, Incorporated of Corning, N.Y. As shown, the heat conductor 30 is captured between the heat generating chamber 22 and the aerosol forming chamber 26 within a narrowed or "necked down" portion of the vessel 20. As a result, the heat conductor 30 medially separates the heat generating chamber 22 and the aerosol forming chamber 26 of the vessel 20. In addition, the heat generating chamber 22 is provided with a stem 21*a* (see FIG. 2 and FIG. 3) for receiving the smaller diameter tip 42 of the heating element 40. The heat conductor 30 is non-combustible and thermally conductive, and may be solid or semi-porous. For example, the heat conductor 30 may be a thin, solid disc made of a thermally conductive metal or an impervious silicon or ceramic. Alternatively, the heat conductor 30 may be a somewhat thicker disc formed from an extremely low porosity filter made of an organic material, such as cellulose acetate, or an inorganic material, such as polypropylene. In some instances, the heat conductor 30 may be an extremely fine wire mesh or perforated metal disc. Typically, the desired thermal conductivity, porosity, thickness and material of the heat conductor 30 will be determined by the volatility of the therapeutic drug and aerosol forming agent deposited on the substrate 50. Regardless, the heat conductor 30 is operable to transfer the heat generated by the heating element 40 within the heat generating chamber 22 to the substrate 50 disposed within the aerosol forming chamber 26 by conduction, convection, or other heat transfer means, as will be readily appreciated by those of ordinary skill in the art. In many instances, the heat conductor 30 is further operable to support the substrate 50 in heat conducting relation within the aerosol forming chamber 26, as will be described in greater detail hereinafter.

The heating element 40 may be any device or apparatus for generating heat, including for example, an electrical heating element (e.g., electrical power source or battery), a mechanical heating element (e.g., friction or magnetic field), a chemical heating element (e.g., chemical reaction) or a combustible fuel heating element, that generates and transfers heat to the heat conductor 30 and/or the substrate 50 by conduction, convection, or other heat transfer means. Furthermore, an electrical heating element may conduct heat directly to the substrate 50, or the substrate may be formed of a conductive material, such as metal that generates resistive heat when subjected to an electrical potential. As shown and further described herein, a preferred embodiment of the heating element 40 generates heat from a fuel source consisting essentially of a combustible liquefied gas, such as liquefied petroleum gas (LPG or LP-Gas), propane, propylene, butylenes, butane, isobutene, methyl propane and n-butane. The combustible liquefied gas comprises hydrocarbons, and in particular, aliphatic hydrocarbons such as carbon alkenes, which are gases at normal atmospheric temperatures and pressures, but are typically compressed to a liquid for storage and transport. The combustible liquefied gas is readily available, economical to use and burns relatively clean compared to carbonaceous and fossil fuels. When ignited in the presence of sufficient oxygen, the combustible liquefied gas burns to produce essentially water vapor ($H_2O$) and carbon dioxide ($CO_2$). When free oxygen is limited, the ignited combustible liquefied gas also produces small amounts of carbon soot and carbon monoxide (CO). As a result, there is little or no opportunity for the patient to inhale any harmful or unhealthy by-products or combustion gases produced by ignition of the heating element 40.

As previously mentioned, the heating element 40 may be any suitable commercially available device or apparatus for generating heat from the combustible liquefied gas. Preferably, the heating element 40 is sufficiently small and lightweight to be held in one or both hands of the patient during delivery of the drug aerosol. The entire aerosol drug delivery device 10, including the heating element 40, should be small enough and lightweight enough to be sufficiently portable such that the patient can transport and use the device anywhere at his or her convenience. Additionally, the heating element 40 may be equipped with means for thermostatically controlling the temperature of the heat in a known manner. The specific type, style and brand of the heating element 40 are not considered to be essential to the invention. Regardless, an existing heating element 40 that has been proven to be suitable to achieve the primary objectives and advantageous of the invention is a Weller® Portasol® PSI 100 handheld butane heat tool available from Cooper Tools of Apex, N.C. "Weller" is a registered trademark of Cooper Industries, Inc. of Apex, N.C. "Portasol" is a registered trademark of Oglesby and Butler Ltd. (c/k/a "O&B, Ltd."). O&B, Ltd. has successfully designed, developed and marketed thermostatically controlled heating elements of the type that are preferred for use with the present invention.

The substrate 50 is disposed within the aerosol forming chamber 26 in any convenient manner such that the substrate is in heat conducting relation with the heat conductor 30. In other words, the substrate 50 is in direct physical contact with the heat conductor 30, or is immediately adjacent the heat conductor, so that heat (i.e., thermal energy) generated by the heating element 40 within the heat generating chamber 22 is transferred across the heat conductor to the substrate. Preferably, the substrate 50 is placed directly onto the upper surface of the heat conductor 30 and below the air inlets 28 to maximize heat conduction to the substrate and delivery of the aerosol drug to the patient. Useful substrates 50 are porous and capable of retaining a therapeutic drug and an aerosol forming agent when not in use, while being capable of releasing the therapeutic drug in a vapor or aerosol form upon the application of heat by the heating element 40. The substrate 50 is made of a thermally stable, non-combustible material having sufficient surface area and/or porosity for the therapeutic drug and aerosol forming agent to be deposited thereon, and to permit vaporization aerosol formation by the application of heat. As used herein, "thermally stable" is intended to mean capable of withstanding the high temperatures (e.g., about 400° C. to about 600° C.) which exist in the vicinity of the heating element 40 within the heat generating chamber 22 without decomposition or burning. Useful thermally stable materials include thermally stable adsorbent carbons, such as porous grade carbons, graphite, activated or non-activated carbons, carbon fibers, carbon yarns, and the like. Other suitable materials include inorganic solids such as ceramics, glass, aluminum pellets, alumina, vermiculite, clays such as bentonite, and the like.

The substrate 50 may have any desired size and shape sufficient to contain at least a single dose amount (in some instances a plurality of dose amounts may be possible) of the therapeutic drug and enough aerosol forming agent to volatilize the therapeutic drug and form the aerosol drug. In one embodiment, the substrate 50 is a generally circular disc formed from a cellulose-based paper material commonly utilized in dentistry that is sold under the trade name DRI-AID and available from The Lorvic Corporation of St. Louis, Mo. It has been found that a generally circular disc of the material having a diameter of about $7/16$ inches and a thickness of about $1/16$ of an inch containing a single drop of an aerosol forming agent consisting essentially of glycerin (about 0.0712 grams) is useful for low temperature vaporization and aerosol formation at temperatures below the decomposition threshold of cellulose. In most instances, it is possible to form the cellulose-based material into a substrate 50 having sufficient surface area to contain the necessary amount of the therapeutic drug and the aerosol forming agent without exceeding the maximum thickness of the substrate suitable for vaporization and aerosol formation by transfer of the heat generated by the heating element 40 through the heat conductor 30 and the substrate. It should be noted that the substrate 50 may be provided in any desired shape, such as circular, cylindrical, rectangular, square, conical, etc., and is described herein as being "disc" shaped by way of example only.

An alternative embodiment of the substrate 50 is shown in FIGS. 4-6 and 6A. FIG. 4 is a top plan view of the substrate 50, while FIG. 5 and FIG. 6 are cross-sectional views of the substrate taken along the lines 5-5 and 6-6 indicated in FIG. 4. FIG. 6A is a detail view of a portion of the substrate indicated in FIG. 6. The alternative embodiment of the substrate 50 shown in FIGS. 4-6 and 6A is intended to significantly increase the amount of surface area available for depositing the therapeutic drug and the aerosol forming agent as compared to a substrate made of a substantially solid material, such as the cellulose disc previously described, having the same diameter and thickness (i.e., volume). The alternative embodiment of the substrate 50 is formed of a finely woven wire mesh material comprising a plurality of layers of wire mesh weaves. An example of such a suitable substrate 50 is a metal filter cloth available from the G. BOPP USA, Inc. of Hopewell Junction, N.Y. A particularly well suited embodiment of the metal filter cloth is commercially known as Twilled Dutch Weave Wire Cloth having a 510×3600 warp-to-weft weave with a warp wire 51 diameter of about 0.025 mm and a weft wire 53 diameter of about 0.015 mm. The preferred BOPP Twilled Dutch Weave Wire Cloth has a nominal filter rating of less than about 1 micron and an absolute filter rating of between about 5 and about 6 microns. The Twilled Dutch Weave Wire Cloth provides extremely small openings to maximize heat conduction and convection, while increasing the surface area available for deposition of the therapeutic drug and aerosol forming agent as much as 4-fold. The specific weave and warp wire/weft wire diameter of the metal filter cloth, however, is determined by the optimum drug delivery characteristics of a particular aerosol drug, and in particular, the boiling point, vaporization rate and aerosol formability of the therapeutic drug and the aerosol forming agent combination.

As previously mentioned, the therapeutic drug and the aerosol forming agent are deposited onto the substrate 50 so that the aerosol forming agent can subsequently volatilize the therapeutic drug to form an aerosol drug when heat is applied to the substrate. As best shown in FIG. 6A, the therapeutic drug and the aerosol forming agent are preferably combined into an admixed solution that is deposited onto the substrate 50. The admixed solution may be deposited onto the substrate in any convenient manner using any conventional means or process. By way of example, and without limitation, the admixed solution 52 may be deposited onto the substrate 50 by coating, spraying, brushing, dipping, vapor deposition, electrostatic deposition, chemical deposition, etc. such that the admixed solution forms a relatively thin film 52 on the substrate consisting essentially of the therapeutic drug and the aerosol forming agent. The therapeutic drug may be any thermally stable, non-combustible drug that is capable of being aerosolized and delivered to a patient by inhalation. As used herein, "thermally stable" is intended to mean capable of withstanding the high temperatures (e.g., about 100° C. to about 400-500° C.) which exist adjacent the heating element 40 within the heat generating chamber 22 without decomposing, burning or otherwise degrading. The aerosol forming agent may be any thermally stable, inert aerosol former and/or drug carrier that is capable of volatilizing the therapeutic drug and forming an aerosol drug suitable for delivery to the patient utilizing an aerosol drug delivery device 10 according to the present invention.

Aerosol forming agents useful in the present invention are capable of forming an aerosol at the temperatures present in the aerosol forming chamber 26 when heat is generated by the heating element 40. Such materials preferably are composed of carbon, hydrogen and oxygen, but they can include other elements and/or compounds. The aerosol forming agent can be in solid, semisolid, or liquid form. Substances having these characteristics include polyhydric alcohols, such as glycerin and propylene glycol, as well as aliphatic esters of mono-, di-, or poly-carboxylic acids, such as methyl stearate, dimethyl dodecandioate, dimethyl tetradecandioate, and others. Preferably, the aerosol forming agent is a polyhydric alcohol, or a mixture of polyhydric alcohols. By way of example, and without limitation, preferred aerosol formers include glycerin, glycerol, propylene glycol, 1,3-butylene glycol, triethylene glycol, glycerol esters, propylene carbonate, and mixtures thereof. As much as possible of the therapeutic drug and the aerosol forming agent carried on the substrate 50 should be delivered to the user as wet total particulate matter (WTPM). Preferably, above about 2 weight percent, more preferably above about 15 weight percent, and most preferably above about 20 weight percent of the admixed solution is delivered to the patient as WTPM. The substrate 50, with the thin film 52 of the admixed solution of the therapeutic drug and the aerosol forming agent deposited thereon may be provided to the patient separately from the device 10 as a single-dose amount of the therapeutic drug. For example, a plurality of substrates 50 may be provided to the patient in the commonly used drug packaging commercially known as a "blister pack" with each substrate vacuum packaged, sealed and individually removable. Therefore, a combination of therapeutic drugs may be delivered to a patient by using a single substrate containing those therapeutic drugs, or by using multiple substrates each containing one or more of those therapeutic drugs.

The aerosol delivery device of the present invention is designed to deliver a therapeutic drug to a patient in the form of an aerosol drug for inhalation therapy in a simple to use, convenient, portable, repeatable and reliable manner. The aerosol drug consists essentially of air, the therapeutic drug and the aerosol forming agent. The aerosol drug may also contain any desired flavorant or inert additive for improving the taste, consistency, and/or texture of the aerosol drug, thereby making the inhalation therapy more palatable. The aerosol drug may also contain chemicals or compounds known as "percutaneous penetration enhancers (PPEs)" that facilitate the rapid transfer of the therapeutic drug into the blood system by enhancing transdermal delivery of the drug. A study of the PPEs found in cigarette mainstream smoke (MS) and their effects is discussed in FOOD AND CHEMICAL TOXICOLOGY 42 (2004) 9-15: *Percutaneous penetration enhancers in cigarette mainstream smoke* co-authored by one of the inventors of the present invention. The aerosol drug should have no significant mutagenic activity as measured by the industry standard Ames test. An aerosol drug delivery device 10 according to the present invention, when used properly, should deliver very low levels of carbon monoxide, preferably less than about 1 mg total CO delivery over the life of the article, more preferably less than about 0.5 mg total CO delivery, and most preferably essentially no total CO delivery.

In operation, the invention may be used in inhalation therapy as a method for delivering a therapeutic drug to a patient in the form of an aerosol. A method according to the present invention includes providing a heat generating chamber 22, as previously described, and an aerosol forming chamber 26, as previously described, separated by a heat conductor 30, as previously described. A heating element 40, as previously described, is disposed within the heat generating chamber 22 in heat conducting relation with the heat conductor 30. If provided separately for increased portability and refurbishment or replacement, the tip 42 of the heating element 40 is positioned within the first end 21 of the heat generating chamber 22. A substrate 50 comprising a therapeutic drug and an aerosol forming agent, as previously described, is disposed within the aerosol forming chamber 26 in heat conducting relation with the heat conductor 30. Prior to or thereafter, the substrate 50 is placed into the aerosol forming chamber 26 through the first end 25 and onto the upper surface of the heat conductor 30. If the mouthpiece 62 is provided, the first end 61 of the aerosol delivery chamber 60 is secured onto the first end 25 of the aerosol forming chamber 26. The heating element 40 is then ignited to generate heat from a fuel source consisting essentially of a combustible liquefied gas within the heat generating chamber 22.

The method further includes conducting the heat generated by the heating element 40 through the heat conductor 30 to the substrate 50. The heat conducted to the substrate 50 activates the aerosol forming agent on the substrate to volatilize the therapeutic drug and the aerosol forming agent disposed on the substrate into an aerosol drug. The aerosol drug containing the therapeutic drug is released into the aerosol forming chamber 26 and, if utilized, into the aerosol delivery chamber 60, where it is made available to be inhaled by the patient. The patient draws air into the aerosol forming chamber 26 through the air inlets 28 and consequently through the first end 25 of the aerosol forming chamber 26 and, if utilized, through the mouthpiece 62 of the aerosol delivery chamber 60 to inhale the aerosol drug. Broadly, the heating element 40 is ignited to generate heat (thermal energy) which is transferred via heat conductor 30 and substrate 50 to the aerosol forming agent deposited on the substance. During a draw on the aerosol forming chamber 26 or the mouthpiece 62 of the aerosol delivery chamber 60, air enters the aerosol forming chamber through the peripheral air inlets 28 and delivers the aerosol drug (comprising essentially, air, the volatilized therapeutic drug and the inert aerosol forming agent) into the mouth of the patient.

Experiments have been performed to demonstrate the efficacy of an aerosol drug delivery device configured according to the present invention. In particular, an initial experiment was performed to determine the mass transfer of various polyols from a substrate consisting of a relatively dense cellulose pad. In this first experiment, an aerosol drug delivery device 10 according to the invention was configured to operate at about 300° C. Two different polyols were tested that generated different Mass Median Aerodynamic Diameter (MMAD) aerosol particles. The device 10 was tested over about a 10 minute time period for the glycerin polyols. The quantity of glycerin tested was from about 98 to about 124 mg, and an average mass transfer of about 40% of the glycerin was measured. The device 10 was tested over about a 5 minute time period at about 300° C. for the propylene glycol polyols. The quantity of propylene glycol tested was from about 50 to about 78 mg, and an average mass transfer of about 80% of the propylene glycol was measured. Although in one case, 100% of the propylene glycol was transferred from the substrate. The results for the first experiment are summarized in the following table.

| Expt. No. | Aerosol Former | Wt of aerosol former on substrate (mg) | Time Device was heated (min) | Total transfer of aerosol from device (%) |
|---|---|---|---|---|
| 1 | Glycerin | 98 | 10 | 47 |
| 2 | Glycerin | 124 | 10 | 36 |
| 3 | Glycerin | 120 | 10 | 34 |
| 4 | Propylene Glycol (PEG) | 50 | 5 | 100 |
| 5 | PEG | 73 | 5 | 62 |
| 6 | PEG | 78 | 5 | 79 |

A subsequent experiment was then performed to determine the mass transfer of various polyol-drug formulations. In this second experiment, the efficacy of an aerosol drug delivery device 10 according to the invention utilizing propylene glycol as the aerosol former was demonstrated. The therapeutic drugs used for the experiment were nicotine (NIC) and nicotine bitartrate (NIC B). Nicotine and nicotine salts (such as NIC and NIC B) are common therapeutic drugs used in the pharmaceutical industry. Nicotine has been suggested for use in the treatment of schizophrenia, Alzheimer's and Parkinson's diseases, and hyperactivity disorders. Nicotine salts are commonly used as drugs in smoking cessation therapies, e.g., Habitrol®, Nicoderm®, Nicorette®, Nicotrol NS®, Prostep®. Nicotine and nicotine bitartrate were selected because of their differences in physical form, volatility, documented thermal degradation characteristics and degradation products, means of trapping, and numerous analytical methodologies for quantification. Furthermore, nicotine is a clear, volatile, liquid, whereas nicotine bitartrate is a non-volatile, white solid. Nicotine is soluble in propylene glycol and nicotine bitartrate is insoluble. Both compounds in the presence of propylene glycol will form an aerosol and the aerosol mixture can be delivered to a patient for therapeutic use. The experiments and the associated analytical analyses were conducted at an independent commercial laboratory, namely Applied Analytical, Inc. of Blacksburg, Va.

Five formulations of NIC and NIC B were prepared, analyzed for nicotine, and applied to a substrate consisting of a relatively dense cellulose pad. Substrates containing 1) no PEG and no drug (substrate only); 2) PEG only; 3) PEG with NIC; and 4) PEG with NIC B were tested in the aerosol drug delivery device 10 using Borgwaldt Technik, RGA System R26 Pneumatic Panel RM 20/CS puffing equipment. The puffing equipment was configured to take about a 129.5 ml. volume puff during about a 2 second interval. One puff was taken every 10 seconds, and 30, 36, or 60 puffs were taken for each experiment. The time for each experiment was either 5 minutes (30 puffs), 6 minutes (36 puffs), or 10 minutes (60 puffs). The shape of each puff was "bell shaped" as opposed to "square-shaped." In particular, the flow was not constant, but instead first increased and then decreased. The effluent from puffs for each experiment was collected on acid-treated Cambridge pads. The mass collected on the Cambridge pad from each experiment was then weighed and used for the determination of total mass transfer. Nicotine was extracted from the Cambridge pads and analyzed using GC/MS. The results for the second experiment are summarized in the following table.

| Expt. No. | Material on substrate disc | Wt of PEG or Polyol-drug (mg) | Time heated (min) | Nicotine analyzed from substrate (mg) | % Mass transfer from substrate | % Mass transfer of nicotine from substrate |
|---|---|---|---|---|---|---|
| 1 | Heated substrate alone | 0 | 5 | 0.0 | — | — |
| 2 | PEG only | 46.7 | 5 | 0.0 | 91.4 | — |
| 3 | PEG w/ NIC | 54.8 | 5 | 1.3 | 81.8 | 81.8 |
| 5 | PEG w/ NIC | 53.6 | 5 | 3.4 | 80.2 | 80.2 |
| 6 | PEG w/ NIC B | 48.3 | 6 | 0.2 | 90.9 | 90.9 |
| 7 | PEG w/ NIC B | 58.2 | 10 | 0.8 | 94.8 | 94.8 |
| 8 | PEG w/ NIC B | 127.9 | 10 | 2.6 | 74.7 | 74.7 |
| | | | | Average | 85.6 | 84.5 |

Drugs tested were nicotine (NIC) or nicotine bitartrate (NIC B).
Puff volume and duration of puffs used in experiments were 129.5 ml and 2 sec, respectively. One puff was taken every 10 seconds.
Percent recovery of nicotine (NIC and NIC B) by GC/MS from polyol-drug formulations on substrate were 97%.

The experimental data indicated that on average about 85.6% of the polyol or polyol-drug formulation deposited on the substrate was transferred and collected. In some instances the mass transfer was over 90%, particularly for those samples where the weight of polyol or polyol-drug were below 50 mg. Longer puffing time appears to improve the mass transfer. Nicotine was monitored as the therapeutic drug in these experiments since NIC B decomposes into nicotine. The mass transfer of nicotine in all cases followed the mass transfer of the polyol and averaged about 84.5%. The GC/MS analysis of the nicotine extracts revealed three distinct peaks; a peak for the solvent used to extract the effluent collected on the pad, a single peak for nicotine, and an organic impurity found on all pads. There were no measurable decomposition products from nicotine (NIC or NIC B) in the chromatograms. The remainder of the mass of the polyol-drug formulation was not accounted for, but may have remained on the substrate, been lost in-between puffs, or could have condensed inside the delivery line prior to collection on the Cambridge pad.

In summary, Polyol-nicotine (PEG-NIC) and polyol-nicotine bitartrate (PEG-NIC B) were tested as representative polyol-drug formulations in an aerosol drug delivery device 10 according to the present invention. The therapeutic drugs varied substantially in physical and chemical form. The mass transfer of the different polyols utilizing the aerosol drug delivery device 10 varied significantly, while the load of polyol or polyol-drug formulation on the substrate 50 is important. Thus, there appears to be an optimal level of polyol or polyol-drug formulation that can be deposited on the substrate 50 based on the desired size of the heat generating chamber 22 and the aerosol forming chamber 26. Any excess polyol or polyol-drug formulation deposited on the substrate 50 decreases the mass transfer of polyol or poyol-drug formulation. The selection of polyol is important due to the MMAD of the aerosol formed from each polyol. For example, glycerin has a larger MMAD compared to propylene glycol. The MMAD for glycerin is reported to be less than about 1.5 micrometers, while the MMAD for PEG is reported to be less than about 0.9 micrometers. The polyols tested in the first experiment exhibit different mass transfer rates based upon the design and dimensions of the aerosol drug delivery device 10. Accordingly, different polyols or combinations of polyols having unique MMADs can be employed depending upon the therapeutic drug to be administered and the desired location for deposition of the therapeutic drug.

The foregoing is a description of various embodiments of the invention that are given here by way of example only. Although an aerosol drug delivery device and method for delivering a therapeutic drug to a patient in the form of an aerosol according to the present invention have been described with reference to preferred embodiments and examples thereof, other embodiments and examples, such as miniaturized versions of the device, may perform similar functions and/or achieve similar results. All such equivalent embodiments and examples are considered to be within the spirit and scope of the present invention and are intended to be encompassed by the appended claims.

That which is claimed is:

1. A device for delivering a therapeutic drug to a patient in the form of an aerosol, the device comprising:
   a heat conductor;
   a heat generating chamber having an open first end and a second end essentially closed by the heat conductor;
   an aerosol forming chamber having an open first end and a second end adjacent the second end of the heat generating chamber and essentially closed by the heat conductor;
   a heating element adapted to be disposed within the heat generating chamber and positioned in heat conducting relation to the heat conductor;
   a substrate adapted to be disposed within the aerosol forming chamber and positioned in heat conducting relation to the heat conductor, the substrate comprising a thermally stable, non-combustible material having the therapeutic drug and an aerosol forming agent deposited thereon; and
   an aerosol delivery chamber adapted to removably engage the open first end of the aerosol forming chamber so as to permit the substrate to be inserted into the aerosol forming chamber in heat conducting relation to the heat conductor for delivery of the therapeutic drug to the patient and to be removed from the aerosol forming chamber thereafter, the aerosol delivery chamber defining a mouthpiece for delivering the therapeutic drug to the patient in the form of an aerosol.

2. The device according to claim 1, wherein the heating element comprises a fuel source consisting essentially of a combustible liquefied gas selected from the group consisting of liquefied petroleum gas (LPG or LP-gas), propane, propylene, butylenes, butane, isobutene, methyl propane and n-butane.

3. The device according to claim 1, wherein the substrate comprises at least one of a cellulose-based paper and a woven wire mesh.

4. The device according to claim 1, wherein the aerosol forming agent is a polyol.

5. The device according to claim 4, wherein the polyol is selected from the group consisting of glycerin, glycerol, propylene glycol, 1,3-butylene glycol, triethylene glycol, glycerol esters, propylene carbonate, and mixtures thereof.

6. The device according to claim 1, wherein the therapeutic drug is a heat stable pharmaceutical having less than about 10% alteration and degradation under normal transport and storage conditions.

7. The device according to claim 1, wherein the aerosol delivery chamber is in sealed relation with the aerosol forming chamber and in spaced relation with the heat conductor, and wherein the mouthpiece is operable for permitting the patient to inhale the therapeutic drug in an aerosol form.

8. The device according to claim 7, further comprising a particle filter disposed between the mouthpiece of the aerosol delivery chamber and the substrate, the particle filter configured to prevent the passage of particles having a mean diameter greater than about 20 microns.

9. The device according to claim 1, wherein the heating element comprises means for thermostatically controlling the temperature of heat generated by the heating element within the heat generating chamber.

10. An aerosol drug delivery device comprising:
   a vessel comprising a heat generating chamber and an aerosol forming chamber separated by a heat conductor;
   a heating element adapted to be disposed within the heat generating chamber in heat conducting relation to the heat conductor;
   a substrate adapted to be disposed within the aerosol forming chamber in heat conducting relation to the heat conductor, the substrate comprising a thermally stable, non-combustible material having a therapeutic drug deposited thereon; and an aerosol delivery chamber comprising a mouthpiece, the aerosol delivery chamber operatively engaging the aerosol forming chamber to permit the substrate to be received within the aerosol forming chamber in heat conducting relation to the heat conductor and to be removed from the aerosol forming chamber;

wherein the heating element generates heat and the heat generated by the heating element volatilizes the therapeutic drug from the substrate in the form of an aerosol drug.

11. An aerosol drug delivery device comprising:
a vessel comprising a heat generating chamber and an aerosol forming chamber separated by a heat conductor;

a heating element adapted to be disposed within the heat generating chamber in heat conducting relation to the heat conductor; and a substrate adapted to be disposed within the aerosol forming chamber in heat conducting relation to the heat conductor, the substrate comprising a thermally stable, non-combustible material having a therapeutic drug and an aerosol forming agent deposited thereon; and an aerosol delivery chamber comprising a mouthpiece, the aerosol delivery chamber operatively engaging the aerosol forming chamber to permit the substrate to be received within the aerosol forming chamber in heat conducting relation to the heat conductor and to be removed from the aerosol forming chamber;

wherein the substrate comprises at least one of a cellulose-based paper and a woven wire mesh.

12. A method of delivering an aerosol drug to a patient comprising:
providing a heat generating chamber and an aerosol forming chamber separated by a heat conductor;
disposing a heating element within the heat generating chamber in heat conducting relation with the heat conductor;
disposing a substrate comprising a thermally stable, non-combustible material having the therapeutic drug and an aerosol forming agent deposited thereon within the aerosol forming chamber in heat conducting relation with the heat conductor;

providing a mouthpiece separate from the substrate that is adapted to removably engage an open end of the aerosol forming chamber so as to permit the substrate to be disposed within the aerosol forming chamber in heat conducting relation with the heat conductor;

igniting the heating element to generate heat;

conducting the heat generated by the heating element through the heat conductor to the substrate; and heat-activating the aerosol forming agent to volatilize an aerosol drug from the therapeutic drug and the aerosol forming agent deposited on the substrate that is released into the aerosol forming chamber and made available to the patient to be inhaled through the mouthpiece.

13. The method according to claim 12, wherein the heating element generates heat from a fuel source consisting essentially of a combustible liquefied gas selected from the group consisting of liquefied petroleum gas (LPG or LP-gas), propane, propylene, butylenes, butane, isobutene, methyl propane and n-butane.

14. The method according to claim 12, wherein the substrate comprises at least one of a cellulose-based paper and a woven wire mesh.

15. The method according to claim 12, wherein the aerosol forming agent is a polyol.

16. The method according to claim 15, wherein the polyol is selected from the group consisting of glycerin, glycerol, propylene glycol, 1,3-butylene glycol, triethylene glycol, glycerol esters, propylene carbonate, and mixtures thereof.

17. The method according to claim 12, wherein the therapeutic drug is a heat stable pharmaceutical having less than about 10% alteration and degradation under normal transport and storage conditions.

18. The method according to claim 12, wherein the mouthpiece is in sealed relation with the aerosol forming chamber and in spaced relation with the heat conductor.

19. The method according to claim 18, further comprising providing a particle filter disposed between the mouthpiece and the substrate, the particle filter configured to prevent the passage of particles having a mean diameter greater than about 20 microns.

20. The method according to claim 12, wherein the heating element comprises means for thermostatically controlling the temperature of heat generated by the heating element within the heat generating chamber.

* * * * *